(12) United States Patent
Scheuing et al.

(10) Patent No.: US 8,765,114 B2
(45) Date of Patent: Jul. 1, 2014

(54) ANIONIC MICELLES WITH CATIONIC POLYMERIC COUNTERIONS METHODS THEREOF

(71) Applicant: The Clorox Company, Oakland, CA (US)

(72) Inventors: David R. Scheuing, Pleasanton, CA (US); Travers Anderson, Pleasanton, CA (US); William L. Smith, Pleasanton, CA (US); Erika Szekeres, Pleasanton, CA (US); Rui Zhang, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 65 days.

(21) Appl. No.: 13/663,962

(22) Filed: Oct. 30, 2012

(65) Prior Publication Data

US 2014/0120056 A1   May 1, 2014

(51) Int. Cl.
*A01N 41/04* (2006.01)
*A01P 1/00* (2006.01)

(52) U.S. Cl.
USPC ..................................................... 424/78.27

(58) Field of Classification Search
None
See application file for complete search history.

(56) References Cited

U.S. PATENT DOCUMENTS

| | | | |
|---|---|---|---|
| 3,620,773 A | | 11/1971 | Gabriel |
| 4,282,109 A | * | 8/1981 | Citrone et al. ............... 510/373 |
| 4,353,806 A | | 10/1982 | Baker et al. |
| 4,764,365 A | | 8/1988 | Boothe et al. |
| 4,772,462 A | | 9/1988 | Boothe et al. |
| 4,898,725 A | | 2/1990 | Giede et al. |
| 4,940,576 A | | 7/1990 | Walsh |
| 5,110,964 A | | 5/1992 | Hiroi et al. |
| 5,158,766 A | | 10/1992 | Greenwald et al. |
| 5,360,571 A | | 11/1994 | Kilgour et al. |
| 5,444,094 A | | 8/1995 | Malik et al. |
| 5,591,708 A | | 1/1997 | Richter |
| 5,631,218 A | | 5/1997 | Allan et al. |
| 5,658,915 A | | 8/1997 | Abe et al. |
| 5,888,957 A | | 3/1999 | Durbut |
| 5,916,859 A | * | 6/1999 | Choy et al. ................... 510/195 |
| 6,080,387 A | | 6/2000 | Zhou et al. |
| 6,107,266 A | | 8/2000 | Borchers et al. |
| 6,184,188 B1 | | 2/2001 | Severns et al. |
| 6,218,346 B1 | | 4/2001 | Sajic et al. |
| 6,242,526 B1 | | 6/2001 | Siddiqui et al. |
| 6,251,849 B1 | | 6/2001 | Jeschke et al. |
| 6,270,754 B1 | | 8/2001 | Zhou et al. |
| 6,358,909 B1 | | 3/2002 | Ochomongo et al. |
| 6,482,392 B1 | | 11/2002 | Zhou et al. |
| 6,524,485 B1 | | 2/2003 | Dubin et al. |
| 6,569,952 B1 | | 5/2003 | Chen et al. |
| 6,716,805 B1 | | 4/2004 | Sherry et al. |
| 6,780,379 B1 | | 8/2004 | Chen et al. |
| 6,913,686 B2 | | 7/2005 | Hilgarth |
| 7,041,630 B1 | | 5/2006 | Vijayarani Barnabas et al. |
| 7,074,459 B2 | | 7/2006 | Stockel |
| 7,229,837 B2 | | 6/2007 | Chen |
| 7,288,514 B2 | | 10/2007 | Knock et al. |
| 7,334,538 B1 | | 2/2008 | Kuhns |
| 7,381,417 B2 | | 6/2008 | Gamez-Garcia |
| 7,470,290 B2 | | 12/2008 | Budd et al. |
| 7,517,568 B2 | | 4/2009 | Bitowft et al. |
| 7,569,533 B2 | | 8/2009 | Lin et al. |
| 7,579,400 B2 | | 8/2009 | Bavouzet et al. |
| 7,608,573 B1 | | 10/2009 | Falk et al. |
| 7,618,931 B1 | | 11/2009 | Scheuing et al. |
| 7,629,305 B1 | | 12/2009 | Lestage et al. |
| 7,700,540 B2 | | 4/2010 | Deleo et al. |
| 7,871,972 B2 | | 1/2011 | Sengupta |
| 7,888,306 B2 | | 2/2011 | Hughes et al. |
| 7,939,486 B2 | | 5/2011 | Falk et al. |
| 7,939,487 B2 | | 5/2011 | Scheuing |
| 7,939,488 B2 | | 5/2011 | Scheuing et al. |
| 7,939,787 B2 | | 5/2011 | Ripley |
| 8,058,837 B2 | | 11/2011 | Beers et al. |
| 2001/0044401 A1 | | 11/2001 | Perkins et al. |
| 2003/0073606 A1 | | 4/2003 | Howell et al. |
| 2003/0114342 A1 | | 6/2003 | Hall |
| 2003/0186830 A1 | | 10/2003 | Godfroid |
| 2004/0013638 A1 | | 1/2004 | Aubay et al. |
| 2004/0052748 A1 | | 3/2004 | Vondruska |
| 2004/0082925 A1 | | 4/2004 | Patel |

(Continued)

FOREIGN PATENT DOCUMENTS

| | | |
|---|---|---|
| EP | 0335404 A2 | 10/1990 |
| EP | 0195895 B1 | 8/1992 |

(Continued)

OTHER PUBLICATIONS

International Search Report, mailed Jan. 11, 2013, from PCT/US 12/63433, filing date Nov. 2, 2012.

(Continued)

*Primary Examiner* — Frederick Krass
*Assistant Examiner* — Celeste A Roney
(74) *Attorney, Agent, or Firm* — Alok Goel

(57) ABSTRACT

The invention relates to a polymer-micelle complex. The polymer-micelle complexes include a negatively charged micelle that is electrostatically bound to a water-soluble polymer bearing a positive charge. The polymer does not comprise block copolymer, latex particles, polymer nanoparticles, cross-linked polymers, silicone copolymer, fluorosurfactant, or amphoteric copolymer. The compositions do not form a coacervate, and do not form a film when applied to a surface.

20 Claims, 1 Drawing Sheet

(56) References Cited

U.S. PATENT DOCUMENTS

| | | |
|---|---|---|
| 2005/0048005 A1 | 3/2005 | Stockel |
| 2005/0054546 A1 | 3/2005 | Glick et al. |
| 2005/0119221 A1 | 6/2005 | Xia et al. |
| 2005/0276778 A1 | 12/2005 | Chen et al. |
| 2006/0211593 A1 | 9/2006 | Hand et al. |
| 2006/0275337 A1 | 12/2006 | Cohen Stuart et al. |
| 2006/0293197 A1 | 12/2006 | Hatano et al. |
| 2006/0293213 A1 | 12/2006 | Uehara et al. |
| 2007/0041932 A1 | 2/2007 | Jeong |
| 2007/0196284 A1 | 8/2007 | Tournier et al. |
| 2008/0242582 A1 | 10/2008 | Sengupta et al. |
| 2009/0036404 A1 | 2/2009 | MacLeod |
| 2009/0048143 A1 | 2/2009 | Iverson et al. |
| 2009/0104430 A1 | 4/2009 | Cordial et al. |
| 2009/0196845 A1 | 8/2009 | Cordial et al. |
| 2010/0160201 A1 | 6/2010 | Scheuing et al. |
| 2010/0234319 A1 | 9/2010 | Yu |
| 2010/0240566 A1 | 9/2010 | Meine |
| 2010/0291169 A1 | 11/2010 | Liesenfeld et al. |
| 2010/0314118 A1 | 12/2010 | Quintero |
| 2011/0010986 A1 | 1/2011 | Alarco |
| 2011/0046033 A1 | 2/2011 | Zhang |
| 2011/0183852 A1 | 7/2011 | Yeung et al. |
| 2011/0236450 A1* | 9/2011 | Scheuing et al. ............ 424/405 |
| 2011/0236582 A1 | 9/2011 | Bennett |

FOREIGN PATENT DOCUMENTS

| | | |
|---|---|---|
| EP | 0472107 B1 | 12/1994 |
| EP | 0422508 B2 | 3/1998 |
| EP | 0904052 B1 | 12/2002 |
| EP | 1779896 B1 | 8/2012 |
| JP | 01132692 A | 5/1989 |
| WO | 9517817 A1 | 7/1995 |
| WO | 9738673 A1 | 10/1997 |
| WO | 9745510 A1 | 12/1997 |
| WO | 9844791 A1 | 10/1998 |
| WO | 0123511 A1 | 4/2001 |
| WO | 2005030282 A1 | 4/2005 |
| WO | 2010106700 A1 | 9/2010 |
| WO | 2010143934 | 12/2010 |

OTHER PUBLICATIONS

Kim et al., Biodegradable Photo-Crosslinked Thin Polymer Networks Based on Vegetable Oil Hydroxy Fatty Acids J Am Oil Chem Soc (2010) 87:1451?1459, entire document.

Mar. 12, 2013; PCT International Search Report PCT/US2012/63436;The Clorox Company.

* cited by examiner

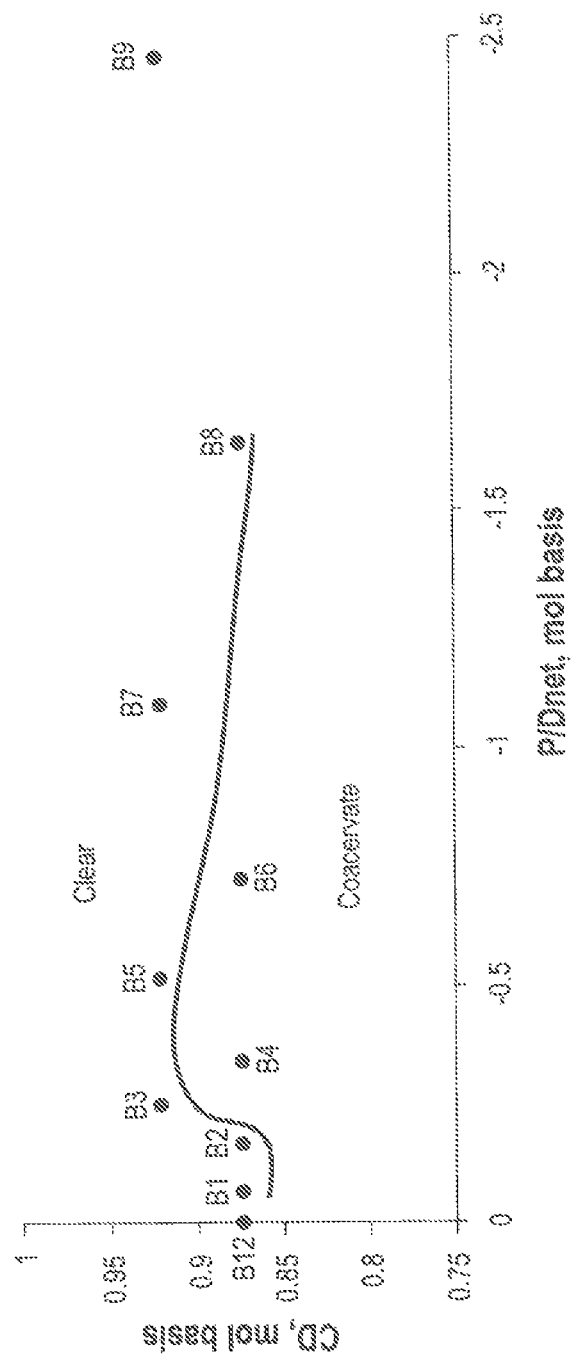

ANIONIC MICELLES WITH CATIONIC POLYMERIC COUNTERIONS METHODS THEREOF

BACKGROUND OF THE INVENTION

1. The Field of the Invention

The present invention relates to polymer-micelle complexes.

2. Description of Related Art

Cleaning product formulations rely on surfactants and mixtures of surfactants to deliver cleaning (detergency), wetting of surfaces, stain removal from fabrics, bleaching of stains, decolorization of mold and mildew, and in some cases, antimicrobial efficacy. A key aspect of these processes is the interaction of the surfactants, oxidants, and antimicrobial agents with the solid surfaces of the materials being cleaned, as well as the surfaces of microorganisms, together with the effects of the formulations on the air-water interface (surface tension). Reduction of the surface tension of aqueous formulations, which is directly related to the effectiveness of the wetting of solid surfaces and hence the detergency and antimicrobial processes, can be manipulated through the use of mixtures of surfactants, as is known in the art.

At a molecular level, surfactants and surfactant mixtures in aqueous media exhibit the ability to adsorb at the air-water, solid-water, and oil-water interfaces, and this adsorption is hence responsible for a wide range of phenomena, including the solubilization of oils in the detergency process, the changes in the properties of solids and dispersions of solids, and the lowering of the surface tension of water. Adsorption of surfactants at interfaces is generally known to increase with surfactant concentration up to a total surfactant concentration known as the critical micelle concentration (CMC). At the CMC, surfactants begin to form aggregates in the bulk solution known as micelles, in equilibrium with the monomeric species of surfactants which adsorb onto the interfaces.

The details of the structures and sizes of the micelles, as well as the properties of the adsorbed layers of surfactants or surfactant mixtures, depend on the details of the molecular shape and charges, if any, on the hydrophilic "headgroups" of the surfactants. Strongly charged headgroups of surfactants tend to repel each other at interfaces, opposing the efficient packing of the surfactants at the interface, and also favoring micelle structures that are relatively small and spherical. The charged headgroups of many surfactants, such as sulfates and sulfonates, will also introduce a counterion of opposite charge, for example a sodium or potassium ion, into formulations.

It is known that the nature of the counterion can affect, the repulsion, between charged surfactants in micelles and adsorbed layers through a partial screening of the headgroup charges from one another in surfactant aggregates like micelles. It is also well known that addition of simple electrolytes, such as sodium chloride, into aqueous solutions can also be used to increase the screening of like headgroup charges from each other, and thus is a common parameter used to adjust the properties of surfactant micelles, such as size and shape, and to adjust the adsorption of surfactants onto surfaces.

Addition of significant amounts of simple electrolytes into many formulations, such as hard surface spray cleaners or nonwoven wipes loaded with a cleaning lotion, is undesirable due to residues left behind open drying of the formulations. An alternative method to adjusting the properties, of such formulations, including the wetting of solid surfaces and stains on them, or the wetting and interactions with microbes, is to include significant amounts of volatile organic solvents such as lower alcohols or glycol ethers. Volatile organic solvents, however, are coming under increasing regulation due to their potential health, effects, and are not preferred by the significant fraction of consumers who desire efficacious cleaning and disinfecting products with a minimum of chemical actives, including volatiles. In the healthcare industry, efficacious formulations comprising lower alcohols are known, bet are viewed as having shortcomings in terms of the potential for irritation of confined patients. Such products pose similar risks to cleaning and clinical personnel who may be exposed to such products or a daily basis.

There is an increasing interest from consumers, and a known need in the healthcare and housekeeping industries, to reduce the number of microorganisms on fabrics while using familiar equipment such as washing machines. Concentrated products are required for such an application, due to the high dilution level of the product in the rinse water, typically by a factor of about 600 times dilution. In the case of formulations comprising quaternary ammonium compounds, high concentrations of the quaternary ammonium compounds in the concentrate are needed in order to ensure an adequate amount of adsorption occurs in a kinetically relevant time onto the microbes under dilution use conditions. As detailed above, it is desirable, yet very difficult, to manipulate (i.e., reduce) the CMC of the quaternary ammonium compound in such an application. Thus very high concentrations of quaternary ammonium compounds, which tend to be hazardous to the skin and eyes, an used in the concentrates, in combination with high temperatures and long exposure times.

Thus, there is an ongoing need for methods and compositions offering fine control of the properties of surfactant aggregates, in order to reduce or eliminate volatile organic solvents. There is also an ongoing need to deliver stain removal and/or antimicrobial activity due to the action of oxidants such as sodium hypochlorite on surfaces which are relatively difficult to wet with lower overall surfactant concentrations.

BRIEF SUMMARY OF THE INVENTION

One aspect of the invention is directed to a method for cleaning a surface. The method comprises contacting a surface with a composition comprising a polymer-micelle complex. The polymer-micelle complex includes a negatively charged micelle electrostatically bound to a water-soluble polymer hearing a positive charge. The water-soluble polymer bearing a positive charge does not comprise block copolymer, latex particles, polymer nanoparticles, cross-linked polymers, silicone copolymer, fluorosurfactant, or amphoteric copolymer. The composition advantageously does not form a coacervate, and is not applied to trapping organic contaminants in a subsurface location.

Another aspect of the invention is directed to a method for treating a surface. The method comprises mixing a first composition comprising a water-soluble polymer having a positive charge with a second composition comprising a negatively charged micelle. The water-soluble polymer bearing a positive charge does not comprise block copolymer, latex particles, polymer nanoparticles, cross-linked polymers, silicone copolymer, fluorosurfactant, or amphoteric copolymer. The composition resulting from mixing of the first and second compositions does not form a coacervate. The method further comprises contacting the resulting composition with a surface so as to treat the surface.

Another aspect of the invention is directed to a method for cleaning a surface. The method comprises contacting, a surface with a composition comprising a polymer-micelle complex. The polymer-micelle complex includes a negatively charged micelle electrostatically bound to a water-soluble polymer bearing a positive charge. The water-soluble polymer bearing a positive charge does not comprise block copolymer, latex particles, polymer nanoparticles, cross-linked polymers, silicone copolymer, flurosurfactant, or amphoteric copolymer. The composition advantageously does not form a coacervate, and is not applied to trapping organic contaminants in a subsurface location. The composition does not comprise alcohols or glycol ethers.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification, it is appreciated that these drawings depict only typical embodiments of the invention and are therefore not to be considered limiting of its scope. The invention will be described and explained with additional specificity and detail through the use of the accompanying drawings in which:

FIG. 1 plots formulations of Example 2 relative to the coacervate phase boundary.

DESCRIPTION OF THE PREFERRED EMBODIMENTS

I. Definitions

Before describing the present invention in detail it is to be understood that this invention is not limited to particularly exemplified systems of process parameters that may, of course, vary, it is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual, publication, patent or patent, application was specifically and individually indicated to be incorporated by reference.

The term "comprising" which is synonymous with "including," "containing," or "characterized by," is inclusive or open-ended and does not exclude additional unrecited elements or method steps.

The term "consisting essentially of" limits the scope of a claim to the specified materials or steps "and those that do not materially affect the basic and novel characteristic(s)" of the claimed invention.

The term "consisting of" as used hereby excludes any elements step, or ingredient not specified in the claim.

It must be noted that, as used in this specification and the appended, claims, the singular forms "a," "an" and "the" include plural referents unless the content clearly dictates otherwise. Thus, for example, reference to a "surfactant" includes one, two or more such surfactants.

The term water-soluble polymer as used hereto means a polymer which gives an optically clear solution free of precipitates at a concentration of 0.001 grams per 100 grams of water, preferably 0.01 grams/100 grams of water, more preferably 0.1 grams/100 grams of water, and even more preferably 1 gram or more per 100 grams of water, at 25° C.

As used herein, the term "substrate" is intended to include any material that is used to clean an article or a surface. Examples of cleaning substrates, include, but are not limited to nonwovens, sponges, films and similar materials which can be attached to a cleaning implement, such as a floor mop, handle, or a hand held cleaning tool such as a toilet cleaning device.

As used herein, the terms "nonwoven" or "nonwoven web" means a web having a structure of individual fibers or threads which are interlaid, but not in an identifiable manner as in a knitted web.

As used, herein, the term "polymer" as used in reference to a substrate (e.g., a nonwoven substrate) generally includes, but is not limited to, homopolymers, copolymers, such, as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("wt %'s") are in wt % (based on 100 weight % active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting, that 1.0 wt % corresponds to 10,000 ppm.

II. Introduction

The present inventors have now determined that the use of water-soluble polymers comprising groups which bear or are capable of bearing an electrostatic charge as counterions (polymeric counterions) for micelles comprising at least one ionic surfactant selected such that the net electrostatic charge on the micelle is opposite to that of the polymeric counterion can yield, simultaneously, very fine control of the interactions between the headgroups of the ionic surfactant as well as the adsorption of the ionic surfactant at the air-liquid and solid-liquid interface when compositions are adjusted such that precipitates or coacervates are completely absent from at least some embodiments of the compositions.

Surprisingly, such compositions in which micelles with polymeric counterions exist as soluble, thermodynamically stable aggregates exhibit very high adsorption activity at both, the air-liquid, and solid-liquid interfaces. Such characteristics completely eliminate the need to adjust formulations such that they change their solubility, forming coacervates or precipitates, in order to deliver adsorption of useful amounts of ionic surfactant and polymer to these interfaces. The micelle-polymer complexes formed when a water-soluble polymer comprising groups which bear or are capable of bearing an electrostatic charge opposite to that of a micelle are usually found to be somewhat larger than the micelles alone. The addition of a water-soluble polymer bearing electrostatic charges opposite to that of at least one surfactant in aqueous solutions often can reduce the CMC of the given surfactant by a significant fraction, which can also have the effect of reducing the cost of certain formulations.

Fine control of surfactant interactions within micelles via addition of oppositely charged polymers according to the invention have also been found to increase the oil solubilization ability of the micelles to an unexpected degree. Without being bound by theory, it is believed that this effect is due to the uniquely high counter ion charge density carried by the charged polymer, which is distinctly different from regular counter ion effect provided by typical salting out electrolytes. This is thought to increase the degree of counter ion association of charged polymers compared to regular electrolytes, even at very low polymer concentrations, which in turn promotes increases in micellar size and an increase in oil solubilization efficiency. The inventors have discovered that the oil solubilization boosting effect develops only if the interactions are fine-tuned such that the system is fully free of coacervate yet is near the water soluble/coacervate phase boundary.

Formulations comprising mixed micelles of an anionic surfactant, optionally a second surfactant such as an amine oxide, and a water-soluble polymer bearing an catonic charge can be made with control of the size and net electrostatic charge. It is believed, without being bound by theory, that the cationic polymers act as polymeric counterions to the anionically charged micelles, either increasing the size of these micelles or collecting groups of these micelles into soluble, thermodynamically stable aggregates which have enhanced activity at solid surface-aqueous solution interfaces, including hard surfaces such as floors, countertops, etc., as well as soft surfaces such as fabrics, non-woven materials, and other surfaces such as the surfaces of microorganisms such as bacteria, viruses, fungi, and bacterial spores. Depending on application use, the surface may be hard, soft, animate (e.g., skin), non-animate, or other type surface.

In one embodiment, the compositions can comprise alcohol, in another embodiment, the compositions can be completely free of water-miscible lower alcohols. Similarly, the compositions can comprise water-miscible glycol ethers or be completely free of the materials, sometimes referred to as "co-solvents" or "co-surfactants". Compositions free of the lower alcohols or glycol ethers not only can provide acceptable antimicrobial performance, at lower cost, but also reduce irritation to patients sub healthcare workers, while providing formulations which can be considered more environmentally friendly or sustainable due to lowered total actives levels and lack of volatile organic compounds. Those embodiments that are free of alcohols or cosolvents may be especially suited as sanitizing cleaners, disinfecting cleaners or treatments for pets in home or veterinary applications.

The compositions may be useful as ready to use cleaners, and may be applied via spraying or pouring, but may also be delivered by loading onto nonwoven substrates to produced pre-moistened wipes. The compositions may also be provided as concentrates that are diluted by the consumer (e.g., with tap water). Such concentrates may comprise a part of a kit for refilling a container (also optionally included within such a kit), such as an empty trigger sprayer. The compositions may also be provided as concentrates for single-use (unit dose) products for cleaning floors, windows, counters, etc. Concentrated dishwashing liquids that provide antibacterial performance upon very high dilutions may be formulated, as may concentrates which can deliver sanitization of laundry via addition to ordinary washloads. Such compositions and results may be achieved without inclusion of triclosan. Such concentrated products also can provide protection against the growth of biofilms and associated outgrowth of molds in drain lines associated with automatic dishwashers, laundry washing machines, and the like, reducing undesirable odors which, are sometimes encountered by consumers.

Concentrated forms of the formulations may also be provided which may be diluted by the consumer to provide solutions that am then used. Concentrated forms suitable for dilution via automated systems, in which the concentrate is diluted with water, or in which two solutions are combined in a given ratio to provide the final use formulation are possible.

The formulations may be in the form of gels delivered to a reservoir or surface with a dispensing device. They may optionally be delivered in single-use pouches comprising a soluble film.

The superior wetting, spreading, aid cleaning performance of the systems make them especially suitable for delivery from aerosol packages comprising either single or dual chambers.

In one embodiment, the compositions do not result in the formation of a durable film on a surface after application. Simple rinsing is sufficient to remove any residue, and even without rinsing, those embodiments of the invention that do form a residue do not form macroscopic durable films. Thus, any remaining residue does not constitute a film, but is easily disturbed, destroyed, or otherwise removed.

The compositions of the present invention are not to be applied or used to trapping organic contaminants in a subsurface location.

III. Definition of Dnet and P/Dnet Parameters

As will be shown in the examples below, very fine control of the interactions between micelles comprising an ionic surfactant and water-soluble polymers bearing electrostatic charges opposite to that of the micelles, and hence functioning as polymeric counterions to the micelles, can be achieved through manipulation of the relative number of charges due to ionic surfactants in the system and those charges due to the water-soluble polymer.

Mixtures of surfactants, including mixtures of ionic and nonionic surfactants, may be employed. A convenient way to describe the net charge on the micelles present in the formulations of the instant invention is to calculate the total number of equivalents of the charged headgroups of the surfactants, both anionic and cationic, followed by a determination of which type of charged headgroup is in excess in the formulation.

Surfactants bearing two opposite electrostatic charges in the formulations, such as carboxy-betaines and sulfo-betaines, act as "pseudo-nonionic" surfactants in the compositions of the instant invention, since me net charge on them will be zero. Thus, the calculation of Dnet will not involve the concentration of such pseudo-nonionic surfactants. Similarly, phosphatidyl choline, an edible material which is a major component of the surfactant commonly referred to as lecithin, contains both an anionically charged phosphate group and a cationically charged choline group in its headgroup region, and thus would be treated as pseudo-nonionic in the inventive compositions. On use other hand, a material such as phosphatidic acid, which contains only an anionically charged phosphate group as its headgroup, would contribute to the calculation of Dnet, as described below.

Some surfactants, such as amine oxides, may be uncharged (nonionic) over a wide range of pH values, but may become charged (e.g., cationically in the ease of amine oxides) at acidic pH values, especially below about pH 5. Although such, components may not contain two permanent and opposite electrostatic charges, applicants have found that they may be treated explicitly as nonionic surfactants in the inventive formulations. As taught herein, inventive compositions which are free of coacervates and precipitates that comprise mixed micelles of an amine oxide and a anionic micelle component and a water-soluble polymer bearing cationic charges may be readily formed through adjustment of the P/Dnet parameter, the Dnet parameter, and/or the presence of adjuvants such as electrolytes, without regard to the precise value of any cationic charge present on the amine oxide.

Two parameters can be defined for any mixture of surfactants comprising headgroups bearing, or capable or bearing, anionic or cationic charges or mixtures of both, said parameters being D anionic and D cationic.

D anionic will be defined as $$D \text{ anionic} = (-1) \times (\text{Eq anionic})$$

D cationic will be defined as $$D \text{ cationic} = (+1) \times (\text{Eq cationic})$$

A final parameter expressing the net charge on the micelles is Dnet, which is simply the sum of the parameters D anionic and D cationic, i.e., $$D\text{net} = D \text{ cationic} + D \text{ anionic}$$

In the expressions above, Eq anionic is the sum of the total number of equivalents or charges due to the headgroups of all anionic surfactants present. For a formulation comprising a single surfactant with a headgroup bearing or capable of bearing an anionic charge;

$$\text{Eq anionic}_1 = (C \text{ anionic}_1 \times Q \text{ anionic}_1)/M \text{ anionic}_1$$

wherein $C$ anionic$_1$ is the concentration of a surfactant with anionic headgroups in grams/per 100 grams of the formulation or use composition, $Q$ anionic$_1$ is a number representing the number of anionic charges present on the surfactant, which may be viewed as having the units equivalents per mole, and $M$ anionic$_1$ is the molecular weight of the surfactant in grams/mole.

For a formulation comprising two different surfactants with anionic headgroups, the parameter Eq anionic would be calculated as the sum:

$$\text{Eq anionic} = \text{Eq anionic}_1 + \text{Eq anionic}_2 = (C \text{ anionic}_1 \times Q \text{ anionic}_1)/M \text{ anionic}_1 + (C \text{ anionic}_2 \times Q \text{ anionic}_2)/M \text{ anionic}_2$$

Commercially available surfactants are often mixtures of materials due to the presence of a distribution in the number of, for example, methylene groups in the hydrophobic "tails" of the surfactant. It is also possible that a distribution in the number of charged "headgroups" per molecule could exist. In practical work wife commercial materials, it may also be acceptable to use an "average" molecular weight or an "average" number of anionic (or cationic) charges per molecule quoted by the manufacturer of the surfactant. In the calculation of D anionic (or D cationic), it may also be acceptable to use values of the Eq anionic (or Eq cationic) derived horn direct analysis of a surfactant raw material.

In the expressions above, Eq cationic is the sum of the total number of equivalents or charges due to the headgroups of all cationic surfactants present. For a formulation comprising a single surfactant with a headgroup bearing or capable of bearing a cationic charge;

$$\text{Eq cationic}_1 = (C \text{ cationic}_1 \times Q \text{ cationic}_1)/M \text{ cationic}_1$$

wherein $C$ cationic$_1$ is the concentration of a surfactant with cationic headgroups in grains/per 100 grams of the formulation or use composition, $Q$ cationic$_1$ is a number representing the number of cationic charges present on the surfactant, which may be viewed as having the units equivalents per mole, and $M$ cationic$_1$ is the molecular weight of the surfactant in grams/mole. In cases where the formulation comprises more than one surfactant with cationic headgroups, the summation of the equivalents of cationic headgroups would be performed as in the case of the anionic surfactants described above.

As an example, consider a formulation comprising a mixture of a single anionic surfactant and a single nonionic surfactant, but lacking a cationic surfactant. Furthermore, consider the anionic surfactant is present at a concentration of 2 wt % or 2 grams/100 grams of the formulation has one group capable of developing an anionic charge per molecule, and has a molecular weight of 200 grams/mole.

Then Eq anionic=(2×1)/200=0.01 equivalents/100 g in the formulation.

Then, D anionic=(−1)×(0.01)x−0.01.

And D cationic=0.

Thus, Dnet=(0−0.01)=−0.01.

As a second example, consider a formulation comprising a mixture of a single anionic surfactant, a single nonionic surfactant, and a single cationic surfactant which is a germicidal quaternary ammonium compound. Furthermore, consider the anionic surfactant is present at a concentration of 2 wt % or 2 grams/100 grams of the formulation, has one group capable of developing an anionic charge per molecule, and has a molecular weight of 200 grams/mole. Furthermore, consider the cationic surfactant is present in the formulation at a concentration 0.1 wt % or 0.1 grams/100 grams of the formulation has one group capable of developing a cationic charge per molecule, and has a molecular weight of 300 grams/mole.

Then Eq anionic=(2×1)/200=0.01 equivalents/100 g in the formulation.

And Eq cationic=(0.1×1)/300=0.00033 equivalents/100 g in the formulation.

Then D anionic=(−1)×(0.01)=−0.01.

And D cationic=(1)×(0.00033)=+0.00033.

Thus, Dnet=+0.00033+(−0.01)=−0.00967. This negative vales clearly indicates that the number of anionically charged headgroups in the mixed micelles comprising the anionic, nonionic, and cationic surfactants present in the formulation exceed that of the cationically charged headgroups.

A second, parameter which can be used to describe the instant invention and the interactions between a polymeric counterion and surfactant micelles bearing a net charge is the ratio P/Dnet.

P is the number of charges (in equivalents) due to the polymeric counterion present per 100 grams of the formulation and can be calculated as follows:

P=(C polymer×F polymer×Q polymer×Z)/M polymer, whom C polymer is the concentration of the polymer in the formulation in grams/100 grams of formulation, F polymer is the weight fraction, of the monomer unit hearing or capable of bearing a charge with respect to the total polymer weight and thus ranges from 0 to 1, Q polymer is the number of charges capable of being developed by die monomer unit capable of bearing a charge and can be viewed as having the units equivalents per mole, Z is an integer indicating the type of charge developed by the monomer unit, and is equal to +1 when the monomer unit can develop a canonic charge or is equal to −1 when the monomer unit can develop an anionic charge, and M polymer is the molecular weight of the monomer unit capable of developing a charge, in grams/mole.

For example, consider a formulation comprising polyacrylic acid homopolymer (PAA) as a water-soluble polymeric counterion. PAA is capable of developing 1 anionic charge per acrylic acid monomer unit (which has a molecular weight of 72 grams/mole), and hence Q polymer=1 and Z=−1. In addition, the polymer is a homopolymer, so F polymer=1. If the PAA is present in the formulation at a concentration of 0.1 grams/100 grams of the formulation, the value of P would be calculated as follows:

$$P=(0.1\times1\times1\times-1)/72=-0.00139.$$

Using the Dnet value of −0.00967 calculated in the example described above for a mixture of an anionic, cationic, and nonionic surfactant, the ratio P/Dnet would be calculated as:

$$P/Dnet=(-0.00139)/(-0.00967)=+\mathbf{0.144}$$

This positive value of P/Dnet not only indicates the ratio of the charges due to the polymeric counterion and the net charge on the mixed micelles, but also indicates, since it is a positive number, that the charge on the polymeric counterion and the net charge on the mixed micelles are the same, both being anionic. In this case, there would be no net electrostatic interaction between the polymeric counterion and the mixed micelles expected, and hence the example would not be within the scope of the instant invention, which requires that the polymeric counterion must be of opposite charge to that of the headgroups of the surfactant or mixture of surfactants comprising the micelle.

As another example, consider a formulation comprising poly(diallyl dimethylammonium chloride) homopolymer (PDADMAC) or poly(DADMAC) as a water-soluble counterion, PDADMAC bears 1 cationic charge per DADMAC monomer unit (which has a molecular weight of 162 gram/mole), and hence Q polymer=1 and Z=+1. In addition, the polymer is a homopolymer, so F polymer=1. If the PDADMAC is present in the formulation at a concentration of 0.1 grams/100 grams of the formulation, the value of P would be calculated as follows:

$$P=(0.1\times1\times1\times1)/162=+0.0006173$$

Using the Dnet value of −0.00967 calculated in the example described above for a mixture of an anionic, cationic, and nonionic surfactant, the ratio P/Dnet would be calculated as:

$$P/Dnet=(+0.0006173)/(-0.00967)=-0.06384.$$

This negative value of P/Dnet not only indicates the ratio of the charges due to the polymeric counterion and the net charge on the mixed micelles, but also indicates, since it is a negative number, that the charge on the polymeric counterion and the net charge on the mixed micelles are opposite. In this case, there may be an electrostatic infraction between the polymeric counterion and the mixed micelles, and hence the formulation may be within the scope of the instant invention.

Alternatively, if the number of equivalents of charged groups present per gram of polymer is available from the manufacturer, or can be derived from the synthetic route used to create the polymer, or can be derived from analysis of the polymer, then P may also be calculated based on that information.

For example, P=(C polymer×Eq polymer×Z), where Cpolymer and Z are defined as above, and Eq polymer is the number of equivalents of groups per gram of polymer with a charge consistent with the value of Z used.

For example, if a water-soluble copolymer that is described as having 0.006173 equivalents per gram of polymer (actives) of a cationically charged monomer, and this polymer is used in a formulation at a concentration of 0.1 grams/100 grams of the formulation, P is calculated as follows:

$$P=(0.1\times0.006173\times1)=+0.0006173.$$

This value of P, with the same Dnet value used in the example above, may then, be used to calculate the ratio P/Dnet $$P/Dnet=(+0.0006173)/(-0.00967)=-0.06384, \text{ which yields the same result as described above.}$$

In the ease of copolymers comprising more than one monomer of like charge or capable of developing a like charge, then the P value calculated for the formulation would be the sum of the P values calculated for each of the appropriate monomers comprising the polymer used.

Finally, in practical work, the absolute value of P/Dnet is an indicator of which charges are in excess and which are in deficiency in formulations of the instant invention. When the absolute value of P/Dnet is greater than 0 but less than 1, the number of charges due to groups on the polymeric counterion is less than the net number of charges due to the headgroups of the ionic surfactant or surfactants comprising the micelles, i.e. the polymeric counterion is in deficiency. When the absolute value of P/Dnet is greater than 1, the polymeric counterion is in excess, and of course, when the absolute value of P/Dnet=1, the number of charges due to the headgroups of the polymeric counterion equals the net number of charges of the ionic surfactant or surfactants comprising the micelles.

IV. Suitable Polymers

Many polymers are suitable for use as polymeric counterions in the instant invention. In one embodiment, the polymers are water-soluble as defined herein. The polymers may be homopolymers or copolymers, and they may be linear or branched. Linear polymers may be preferred in at least some embodiments. Copolymers may be synthesized by processes expected to lead to statistically random or so-called gradient type copolymers. In contrast, water-soluble block copolymers are not suitable, since these types of polymers may form aggregates or micelles, in which the more hydrophobic block or blocks comprise the core of the aggregates or micelles and the more hydrophilic block comprises a "corona" region in contact with water. It is thought that these self-assembly processes compete with the electrostatic, interactions required for a water-soluble polymer to serve as a polymeric counterion with ordinary surfactant micelles. Although mixtures of water-soluble polymers are suitable in at least some embodiments of the present invention, the mixtures selected should not comprise block copolymers capable of forming so-called "complex coacervate" micelles through self-assembly, since, this micelle formation process also competes with the interaction of the water-soluble polymer as a polymeric counterion to ordinary surfactant micelles. When the polymers are copolymers, the ratio of the two or more monomers may vary over a wide range, as long as water solubility of the polymer is maintained.

In an embodiment, the polymers should be water soluble, as defined herein, and therefore, should not be latex particles or microgels of any type. In such embodiments the polymers should, not be cross-linked through the use of monomers capable of forming covalent bonds between, independent polymer chains, and the compositions and formulations should be free of cross-linking agents added expressly for this purpose. It is believed that polymer aggregates that may be "swollen" by wafer in the form of microgels or polymers that form cross-linked networks will not have the appropriate full mobility of the polymer chains needed for them to function as polymeric counterions with respect to ordinary surfactant micelles. Polymer particles which can serve as structurants for an aqueous composition through the formation of fibers or threads are not suitable as the water-soluble polymers for similar reasons. Similarly, latex particles are believed to not be suitable because many of the individual polymer chains in such particles are. In fact, confined to the particle interior and are not readily available for interaction with the aqueous phase. Latex particles also lack the chain mobility required to function as counterions to ordinary surfactant micelles.

The random copolymers may comprise one or more monomers bearing the same charge or capable of developing the same charge and one or more monomers which are nonionic, i.e., not capable of bearing a charge. Copolymers may be synthesized by graft processes, resulting in "comb-like" structures.

Water-soluble copolymers derived from a synthetic monomer or monomers chain terminated with a hydroxyl-containing natural material, such as a polysaccharide, which can be synthesized with ordinary free-radical initiators are preferred. At least one of the synthetic monomers may bear or be capable of bearing a cationic charge. Methods of producing such copolymers are described in U.S. Pat. No. 8,058,374, herein incorporated by reference in its entirety.

In one embodiment, the compositions are free of copolymers comprising at least one monomer bearing or capable of developing an anionic charge and at least one monomer bearing or capable of developing a cationic charge. Such, copolymers, sometimes referred to as "amphoteric" copolymers, are believed to not function as well or at all as polymeric counterions to micelles bearing a net electrostatic charge for at least two reasons. First, the proximity of both types (anionic and cationic) of charges along the polymer chains, if randomly distributed, interferes with the efficient pairing of a given, type of charge on the polymer chain with the headgroup of a surfactant of opposite charge in a micelle. Second, such copolymers have the potential for electrostatic interactions of the anionic charges on a given polymer chain with the cationic charges on another polymer chain. Such interactions could lead to the formation of polymer aggregates or complexes in a process that is undesirably competitive with the interaction of the polymer with micellar aggregates.

The suitable water-soluble polymers may include natural or sustainable materials bearing or capable of developing cationic charges, such as chitosan and its derivatives. Chitosan is advantageously a natural or sustainable material. The water-soluble polymers may also include derivatives of natural polymers such as guar bearing added cationic groups, e.g., quaternized guars, such as Aquacat, commercially available from Hercules/Aqualon.

Suitable water-soluble polymers bearing or capable of bearing a cationic charge may be derived from synthetic monomers. Non-limiting examples of monomers bearing or capable of bearing a cationic charge include diallyl dimethyl ammonium chloride, quaternary ammonium salts of substituted acrylamide, methylacrylamide, acrylate and methacrylate, quaternized alkyl amino acrylate esters and amides, MAPTAC (methacrylamido propyl trimethyl ammonium chlorides), trimethyl ammonium methyl methacrylate, trimethyl ammonium propyl methacrylamide, 2-vinyl N-alkyl quaternary pyridinium salts, 4-vinyl N-alkyl quaternary pyridinium salts, 4-vinylbenzyltrialkylammonium salts, 2-vinyl piperidinium salts, 4-vinyl piperidinium salts, 3-alkyl 1-vinyl imidazolium salts and mixtures thereof. Ethyleneimine is an example of a monomer capable of developing a charge when the pH is suitably reduced. Other suitable cationic monomers include the ionene class of internal cationic monomers.

Non-limiting examples of monomers which are nonionic not bearing, or not capable of bearing an electrostatic charge include the alkyl esters of acrylic acid methacrylic acid, vinyl alcohol, vinyl methyl ether, vinyl ethyl ether, ethylene oxide, propylene oxide, and mixtures thereof. Other examples include acrylamide, dimethylacrylamide, and other alkyl acrylamide derivatives and mixtures thereof. Other suitable monomers may include ethoxylated esters of acrylic acid or methacrylic acid, the related tristyryl phenol ethoxylated esters of acrylic acid or methacrylic acid and mixtures thereof. Other examples of nonionic monomers include saccharides such as hexoses and pentoses, ethylene glycol, alkylene glycols, branched polyols, and mixtures thereof.

In some embodiments, water-soluble polymers comprising monomers which bear N-halo groups, for example, N—Cl groups, are not present. It is believed that interactions between polymers comprising such groups as polymeric counterions to micelles leads to either a degradation of the surfactants themselves and/or a degradation of the polymers through the enhanced local concentration of the polymers at the micelle surfaces.

When the compositions comprise surfactant micelles with for example, a net anionic charge and a water-soluble polymer or mixture of polymers hearing or capable of bearing cationic charges, then the compositions may be free of any additional polymers bearing an anionic charge, i.e., a charge opposite to that of the first water-soluble polymer bearing or capable of bearing cationic charges. The presence of a first water-soluble polymer bearing art cationic charge and a second water-soluble polymer bearing a anionic charge in the same formulation is believed to give rise to the formation of complexes between the two polymers, i.e., so-called polyelectrolyte complexes, which would undesirably compete with the formation of complexes between the micelles bearing the anionic charge and the polymer bearing the cationic charge.

However, compositions comprising surfactant micelles bearing a net electrostatic charge and a water-soluble polymer hearing or capable of bearing an electrostatic charge opposite to that of the surfactant micelles, may comprise additional polymers which do not bear charges, that is, nonionic polymers. Such nonionic polymers may be useful as adjuvants for thickening, gelling, or adjusting the theological, properties of the compositions or for adjusting the aesthetic appearance of the formulations through the addition of pigments or other suspended particulates. It should be noted, however, that in many cases, the polymer-micelle complexes of the instant invention, when, adjusted to certain, total actives concentrations, may exhibit "self-thickening" properties and not explicitly require an additional polymeric thickener, which is desirable from a cost standpoint.

V. Suitable Surfactants

In one embodiment, the compositions are free of nonionic surfactants which comprise blocks of hydrophobic and hydrophilic groups, such as the Pluronic®. It is believed that the micellar structures formed with such large surfactants, in which the hydrophobic blocks assemble into the core regions of the micelles and the hydrophilic blocks are present at the micellar surface would interfere with the polymeric counterion interactions with an additional charged surfactant incorporated into a mixed micelle, and/or also represent a more competitive micelle assembly mechanism, in a manner similar to that of the use of block copolymers used as polymeric counterions which are also preferably not present.

A very wide range of surfactants and mixtures of surfactants may be used, including anionic, nonionic and cationic surfactants and mixtures thereof. As alluded to above in the description of Duet and P/Dnet, it will be apparent that mixtures of differently charged surfactants may be employed. For example, mixtures of cationic and anionic surfactants, mixtures of cationic and nonionic, mixtures of anionic and nonionic, and mixtures of cationic, nonionic and anionic may be suitable for use.

Examples of cationic surfactants include, but are not limited to monomeric quaternary ammonium compounds, monomeric biguanide compounds, and combinations thereof. Suitable exemplary quaternary ammonium compounds are available from Stepan Co under the tradename BTC® (e.g., BTC® 1010, BTC® 1210, BTC® 818, BTC® 3358). Any other suitable monomeric quaternary ammonium compound may also be employed. BTC® 1010 and BTC® 1210 are described as didecyl dimethyl ammonium chloride and a mixture didecyl dimethyl ammonium chloride and n-alkyl dimethyl benzyl ammonium chloride, respectively. Examples of monomeric biguanide compounds include, but are not limited to chlorhexidine, alexidine and salts thereof.

Examples of anionic surfactants include, but are not limited to alkyl sulfates, alkyl sulfonates, alkyl ethoxysulfates, fatty acids and fatty acid salts, linear alkylbenzene sulfonates (LAS and HLAS), secondary alkane sulfonates (for example Hostapur®SAS-30), methyl ester sulfonates (such as Stepan® Mild. PCL from Stepan Corp), alkyl sulfosuccinates, and alkyl amino acid derivatives. Rhamnolipids bearing anionic charges may also be used, for example, in formulations emphasizing greater sustainability, since they are not derived from petroleum-based materials. An example of such a rhamnolipid is JBR 425, which is supplied as an aqueous solution with 25% actives, from Jenil Biosurfactant Co., LLC (Saukville, Wis., USA).

So-called "extended chain surfactants", are preferred in some formulations. Examples of these anionic surfactants are described in. US Pat. Pub. No. 2006/0211593. Non-limiting examples of nonionic surfactants include alkyl amine oxides (for example Ammmonyx® LO from Stepan Corp.) alkyl amidoamine oxides (for example Ammonyx LMDO from Stepan Corp.), alkyl phosphine oxides, alkyl polyglycosides and alkyl polypentosides, alkyl poly(glycerol esters) and alkyl poly(glycerol ethers), and alkyl and alkyl phenol ethoxylates of all types. Sorbitan esters and ethoxylated sorbitan esters are also useful nonionic surfactants. Other useful nonionic surfactants include fatty acid amides, fatty acid monoethanolamides, fatty acid diethanolamides, and fatty acid isopropanolamides.

In one embodiment, a phospholipid surfactant may be included. Lecithin is an example of a phospholipid.

In one embodiment, synthetic zwitterionic surfactants may be present. Non-limiting examples include N-alkyl betaines (for example Amphosol® LB from Stepan Corp.), and alkyl sulfo-betaines and mixtures thereof.

In one embodiment, at least some of the surfactants may be edible, so long as they exhibit water solubility or can form mixed micelles with edible nonionic surfactants. Examples of such edible surfactants include casein and lecithin.

In one embodiment, the surfactants may be selected based on green or natural criteria. For example, there is an increasing desire to employ components that are naturally-derived, naturally-processed, and biodegradable, rather than simply being recognized as safe. For example, processes such as ethoxylation, may be undesirable where it is desired to provide a green or natural product, as such processes can leave residual compounds or impurities behind. Such "natural surfactants" may be produced using processes perceived to be more natural or ecological, such as distillation, condensation, extraction, steam distillation, pressure cooking and hydrolysis to maximize the purity of natural ingredients. Examples of such "natural surfactants" that may be suitable for use are described in U.S. Pat. Nos. 7,608,573, 7,618,931, 7,629,305, 7,939,486, 7,939,488, all of which are herein incorporated by reference.

VI. Suitable Adjuvants

A wide range of optional adjuvant or mixtures of optional adjuvants may be present. For example, builders and chelating agents, including but not limited to EDTA salts, GLDA, MSG, gluconates, 2-hydroxyacids and derivatives, glutamic acid and derivatives, trimethylglycine, etc. may be included.

Amino acids and mixtures of amino acids may be present, as either racemic mixtures or as individual components of a single chirality.

Vitamins or vitamin precursors, for example retinal, may be present.

Sources of soluble zinc, copper, or silver ions may be present, as the simple inorganic salts or salts of chelating agents, including, but not limited to, EDTA, GLDA, MGDA, citric acid, etc.

Dyes and colorants may be present. Polymeric thickeners, when used as taught above, may be present.

Buffers, including but not limited to, carbonate, phosphate, silicates, borates, and combinations thereof may be present. Electrolytes such as alkali metal salts, for example including, but not limited to, chloride salts (e.g., sodium chloride, potassium chloride), bromide salts, iodide salts, or combinations thereof may be present.

Water-miscible solvents may be present in some embodiments. Lower alcohols (e.g., ethanol), ethylene glycol, propylene glycol, glycol ethers, and mixtures thereof with water miscibility at 25° C. may be present in some embodiments. Other embodiments will include no lower alcohol or glycol ether solvents. Where such solvents are present, some embodiments may include them in only small amounts, for example, of not more than 5% by weight, not more than 3% by weight, or not more than 2% by weight.

Water-immiscible oils may be present, being solubilized into the micelles. Among these oils are those added as fragrances. Preferred oils are those that are from naturally derived sources, including the wide variety of so-called essential oils derived from a variety of botanical sources. Formulations intended to provide antimicrobial benefits, coupled with improved, overall sustainability may advantageously comprise quaternary ammonium compounds and/or monomeric biguanides such as water soluble salts of chlorhexidine or alexidine in combination with essential oils such as thymol and the like, preferably in the absence of water-miscible alcohols.

In one embodiment, the composition may further include one or more oxidants. Examples of oxidants include, but are not limited to hypohalous acid, hypohalite and sources thereof (e.g., alkaline metal salt and/or alkaline earth metal salt of hypochlorous or hypobromous acid), hydrogen peroxide and sources thereof (e.g., aqueous hydrogen peroxide, perborate and its salts, percarbonate and its salts, carbamide peroxide, metal peroxides, or combinations thereof), peracids, peroxyacids, peroxoacids (e.g. peracetic acid, percitric acid, diperoxydodecanoic acid, peroxy amido phthalamide, peroxomonosulfonic acid, or peroxodisulfamic acid) and sources thereof (e.g., salts (e.g., alkali metal salts) of peracids or salts of peroxyacids such as peracetic acid, percitric acid, diperoxydodecanoic acid sodium potassium, peroxysulfate, or combinations thereof), organic peroxides and hydroperoxides (e.g. benzoyl peroxide) peroxygenated inorganic compounds (e.g. perchlorate and its salts, permanganate and its salts and periodic acid and its salts), solubilized chlorine, solubilized chlorine dioxide, a source of free chlorine, acidic sodium chlorite, an active chlorine generating compound, or a chlorine-dioxide generating compound, an active oxygen generating compound, solubilized ozone, N-halo compounds, or combinations of any such oxidants. Additional examples of such oxidants are disclosed in U.S. Pat. No. 7,517,568 and U.S. Publication No. 2011/0236582, each of which is herein incorporated by reference in its entirety.

Water-soluble hydrotropes, sometimes referred to as monomeric organic electrolytes, may also be present. Examples include xylene sulfonate salts, naphthalene sulfonate salts, and cumene sulfonate salts.

Enzymes may be present, particularly when the formulations are tuned for use as laundry detergents or as cleaners for kitchen and restaurant surfaces, or as drain openers or drain maintenance products.

Applicants have found that a wide range surfactant mixtures resulting in a wide range of Dnet values may be used. In many cases, the surfactants selected may be optimized for the solubilization of various water-immiscible materials, such as fragrance oils, solvents, or even the oily soil to be removed front a surface with a cleaning operation. In the cases of the design of products which deliver an antimicrobial benefit in the absence of a strong oxidant such as hypochlorite, a germicidal quaternary ammonium compound or a salt of a monomeric biguanide such as chlorhexidine or alexidine are often incorporated, and may be incorporated into micelles with polymeric counterions. The fine control over the spacing between the cationic headgroups of the germicidal quaternary ammonium compound or biguanide which is achieved via the incorporation of a polymeric counterion can result in a significant reduction in the amount of surfactant needed to solubilize an oil, resulting in cost reductions and improvement in the overall sustainability of the formulations.

In contrast to what is described in the art, applicants have also found that the magnitude and precise value of P/Dnet needed to ensure the absence of precipitates and/or coacervate phases can vary widely, depending on the nature of the polymeric counterion and the surfactants selected to form the mixed micelles. Thus, since there is great flexibility in the selection of the polymeric counterion for a given surfactant mixture to achieve a particular goal applicants have adopted a systematic, but simple approach for quickly "scanning through" ranges of P/Dnet, in order to identify, and to compare, formulations comprising polymeric counterions.

The formulations comprising the mixed micelles of a net charge and a water-soluble polymer bearing charges opposite to that of the micelles are useful as ready to use surface cleaners delivered via pre-moistened nonwoven substrates (e.g., wipes), or as sprays in a variety of packages-familiar to consumers.

Concentrated forms of the formulations may also be developed which may be diluted by the consumer to provide solutions that are then used. Concentrated forms that suitable for dilution via automated systems, in which the concentrate is diluted with water, or in which two solutions are combined in a given ratio to provide the final use formulation are possible.

The formulations may be in the form of gels delivered to a reservoir or surface with a dispensing device. They may optionally be delivered in single-use pouches comprising a soluble film.

The superior wetting, spreading, and cleaning performance of the systems make them especially suitable for delivery from aerosol packages comprising either single or dual chambers.

When the compositions comprise chlorhexidine or alexidine salts as a cationically charged surfactant, the compositions may be free of iodine or iodine-polymer complexes, nanoparticles of silver, copper or zinc, triclosan, p-chloromethyl xylenol, monomeric pentose alcohols, D-xylitol and its isomers, D-arabitol and its isomers, aryl alcohols, benzyl alcohol, and phenoxyethanol.

VI. Suitable Nonwoven Substrates

Many of the compositions are useful as liquids or lotions that may be used in combination with nonwoven substrates to produce pre-moistened wipes. Such wipes may be employed as disinfecting wipes, or for floor cleaning in combination with various tools configured to attach to the wipe.

In one embodiment, the cleaning pad of the present invention comprises a nonwoven substrate or web. The substrate may be composed of nonwoven fibers or paper.

VII. Examples

How Particle Size and Zeta Potentials were Measured

The diameters of the aggregates with the polymeric counterions (in nanometers) and their zeta potentials were measured with a Zetasizer ZS (Malvern Instruments). This instrument utilizes dynamic light scattering (DLS, also known as Photon Correlation spectroscopy) to determine the diameters of colloidal particles in the range from 0.1 to 10000 nm.

The Zetasizer ZS instrument offers a range of default parameters which can be used in the calculation of particle diameters from the raw data (known as the correlation function or autocorrelation function). The diameters of the aggregates reported herein used a simple calculation model, in which the optical properties of the aggregates were assumed to be similar to spherical particles of polystyrene latex particles, a common calibration standard used for more complex DLS experiments, in addition, the software package supplied with the Zetasizer provides automated analysis of the quality of the measurements made in the form of "Expert Advice" The diameters described herein (specifically what is known as the "Z" average particle diameter) were calculated from raw data that met "Expert Advice" standards consistent with acceptable results, unless otherwise noted. In other words, the simplest set of default measurement conditions and calculation parameters were used to calculate the diameters of all of the aggregates described herein, in order to facilitate direct comparison of aggregates based on a variety of polymeric counterions and surfactants, and avoiding the use of complex models of the scattering which could complicate or prevent comparisons of the diameters of particles of differing chemical composition. Those skilled in the art will appreciate the particularly simple approach taken here, and realize that it is useful in comparing and characterizing complexes of micelles and water-soluble polymers, independent of the details of the types of polymers and surfactants utilized to form the complexes.

This instrument calculates the zeta potential of colloidal particles from measurements of the electrophoretic mobility, determined via a Doppler laser velocity measurement. There exists a relationship between the electrophoretic mobility (a measurement of the velocity of a charged colloidal particle moving in an electric field) and the zeta potential (electric charge, expressed in units of millivolts). As in the particle size measurements, to facilitate direct comparison of aggregates based on a variety of polymeric counterions and surfactants, the simplest set of default measurement conditions were used, i.e., the aggregates were assumed to behave as polystyrene latex particles, and the Smoluchowski model relating the electrophoretic mobility and the zeta potential was used in all calculations. Unless otherwise noted, the mean zeta potentials described herein were calculated from raw data that met "Expert Advice" standards consistent with acceptable results. Aggregates bearing a net cationic (positive) charge will exhibit positive values of the zeta potential (in mV), while those bearing a net anionic (negative) charge will exhibit negative values of the zeta potential (In mV).

Example 1

Ready to Use Cleaner with Sodium Hypochlorite

A series of formulations at various P/Dnet values were prepared for visual evaluation of phase stability, followed by measurement of the Z-average diameters of the aggregates formed via dynamic light scattering. The formulations are useful as hard surface cleaners, for example for bathroom surfaces or kitchen counters, that are stained by mold or mildew or with tenacious food residues that require the cleaning action of surfactants combined with the stain removal benefits provided by sodium hypochlorite bleach. A control formulation comprising mixed micelles of net anionic charge without the presence of poly(DADMAC) as the polymeric counterion was also made. The formulations, were made by simple mixing of appropriate volumes of aqueous stock solutions of the surfactants, polymer, the sodium carbonate (which provides significant buffer capacity and which keeps the pH of the final formulations within a desirable range), and a source of sodium hypochlorite aqueous solution. The compositions are summarized in Table 1.1.

Ammonyx® LO (amine oxide, Stepan Co.) supplied as active solution in water.

Dowfax™ 2A1 (Dow Corp), supplied as 45% active solution in water, and with an average of 2 sulfonate groups per molecule (Q anionic=2).

PDADMAC=poly(diallyl dimethyl ammonium chloride), Floquat FL4245 (SNF Corp.), supplied as 40% active solution in water, Z polymer=1, Q polymer=1, M polymer=162, F polymer=1 (homopolymer).

NaOCl source=Clorox germicidal bleach, titrated immediately prior to use to determine the sodium hypochlorite activity.

TABLE 1.2

Z-average diameters of Micelles with Polymeric Counterions (Polymer-Micelle Complexes) and Control Micelles Determined by Dynamic Light Scattering at 25° C.

| Formulation Name | Absolute Value, P/Dnet | Z-average diameter, nm (% relative standard deviation at n = 3) |
|---|---|---|
| A1 | 0.169 | 44.41 (1.47) |
| A2 | 0.346 | 56.97 (0.75) |
| A3 | 1.644 | 71.92 (0.201) |
| A4 | 26.306 | 49.21 (1.08) |
| A5 | 0 | 35.8 (0.396) |

The results in Table 1.2 indicate that the addition of poly (DADMAC) as a polymeric counterion for the mixed micelles comprising the amine oxide and sulfonate results in the formation of complexes (formulations A1 through A4) which have larger Z-average diameters than the mixed micelles themselves (formulation A5). The results also indicate that the default parameters selected for calculation of the diameters from the DLS measurements, as described above, gave very reproducible results. For the triplicate analyses of the formulations, the variation between individual Z-average diameters was typically less than 2% relative. Hence, the diameters calculated for formulations A1 through A5. In another experiment demonstrating the reproducibility of the Z-average diameters calculated from the dynamic light scattering data, a sample of formulation A5 was loaded into a sealed disposable cuvette and was analyzed every 30 minutes upon storage in the instrument (with the temperature controlled to 25° C.) overnight. The mean Z-average diameter from 27 separate analyses was 35.96 nm, with a standard deviation of 0.1907, or a percent relative standard deviation of 0.53%. Herein below, Z-average diameters quoted will be the result of at least 3 analyses of a sample. Relative differences of at least 2% relative in the Z-average diameters measured for different formulations will be considered significant, unless the measurement conditions dictate otherwise.

TABLE 1.1

| Formulation Name | wt % Ammonyx® LO | wt % Dowfax™ 2A1 | wt % Na$_2$CO$_3$ | wt % NaOCl | wt % PDADMAC | P/Dnet | Appearance at 25° C. |
|---|---|---|---|---|---|---|---|
| A1-2 | 0.7098 | 0.2652 | 2.5 | 0.9984 | 0.025 | −0.169 | Clear |
| A2-4 | 0.6916 | 0.2584 | 2.5 | 0.9984 | 0.05 | −0.346 | Clear |
| A3-8 | 0.5824 | 0.2176 | 2.5 | 0.9984 | 0.2 | −1.644 | Clear |
| A4-11 | 0.1456 | 0.0544 | 2.5 | 0.9984 | 0.8 | −26.306 | Clear |
| A5-12 | 0.728 | 0.272 | 2.5 | 0.9984 | 0 | 0 | Clear |
| A6-6 | 0.6552 | 0.2448 | 2.5 | 0.9984 | 0.1 | −0.731 | Cloudy (clear at 24° C. and lower) |
| A7-10 | 0.1272 | 0.0728 | 2.5 | 0.9984 | 0.8 | −19.657 | Cloudy |

It is believed, without being bound by theory, that the Z-average diameter of the mixed micelles in formulation A5 is, at 35.8 nm, indicative of the formation of rod-like micelles, due to the relatively high concentration of electrolyte (carbonate buffer, sodium hypochlorite and the sodium chloride present in the sodium hypochlorite stock solution).

In some embodiments, formulations of the instant invention are free of precipitates and coacervate phases. As shown above, adjustment of the P/Dnet parameter can be made, by changing either the concentration of the polymeric counterion or by changing the composition of the mixed micelles by changing the relative amounts of the anionically charged, surfactant and any uncharged surfactant present, or even by changing the relative amounts of an anionically charged surfactant and a cationically charged surfactant present in the formulation. Visual examination of the formulations for clarity is generally sufficient for identifying samples which are clear and free of coacervates and precipitates. However, analysis of samples via dynamic light scattering can also be very useful in confirming the thermodynamic stability of the soluble polymer-micelle complexes formed by the interaction of micelles bearing an electrostatic charge and a water-soluble polymer bearing an electrostatic charge opposite to that of the micelles, in an embodiment, the polymer-micelle complexes should exhibit Z-average diameters of less than about 500 nm, in order to exhibit colloidal stability.

Example 2

Formulations with Sodium Hypochlorite Adjustment of Mixed Micelle Compositions

In this example, formulations comprising mixed micelles of a nonionic amine oxide surfactant and an anionically charged surfactant and poly(DADMAC) as the cationic polymeric counterion, in combination with the oxidant sodium hypochlorite, which exhibit excellent wetting and stain removal performance are provided.

The formulations in this example have a fixed total surfactant+polymer concentration, carbonate buffer, and bleach concentration, and cover a wide range of the absolute value of P/Dnet. As described above, the formulations of the instant invention are free of coacervates and precipitates. That said, formulations that are relatively nearer to a coacervate phase boundary may be preferred due to their relatively faster rates of spreading on both polar and non-polar surfaces, which also results in more rapid stain removal by the oxidant.

Aqueous formulations were prepared by mixing appropriate amounts of stock solutions made with the individual ingredients, Dowfax™ 2A1 sulfonate surfactant (supplied as aqueous solution, Dow Chemical), Ammonyx® LO amine oxide, Sodium carbonate (supplied by Fluka), hypochlorite bleach, Floquat FL 4245 (Cationic polymer, a homopolymer of diallyl dimethyl ammonium chloride or poly(DADMAC) supplied as aqueous solution, SNF International) and water to form the final formulations. The compositions were systematically varied by increasing the overall surfactant charge dilution parameter (CD) values at a given, fixed polymer concentrations until solutions which were clear and free of coacervate were obtained.

The overall surfactant charge dilution parameter, CD, is defined as:

$$CD = C_{uncharged}/(C_{uncharged} + C_{charged})$$

where $C_{uncharged}$ is the molar concentration of the uncharged surfactant and $C_{charged}$ is the molar concentration of the charged surfactant.

Sample B1 represents the formulation optimised at 0.01% polymer and 1% total surfactant+polymer. Sample B2 represents another formulation again optimized to be free of coacervate while maintaining the total surfactant+polymer again at 1%. Sample B3 represents an alternative formulation which is also clear and free of coacervate.

Sample B4 represents a formulation which was observed to be cloudy at about 25° C., but which was clear at lower temperatures, and hence may not be sufficiently robust. However, an alternative formulation (Sample B5) with better stability can be readily provided through a slight change in the CD parameter. Note too that the P/Dnet parameters for all of the formulations are negative, indicating that the polymeric counterion and the mixed micelles are of opposite charges, and hence within the scope of the instant invention.

After mixing the stock solutions the samples were agitated for a few hours and were visually inspected to detect the presence or absence of coacervate phases. At lower overall surfactant charge dilution parameter (CD) values the interaction between the positively charged polymer and the anionic surfactant is strong, leading to coacervation. At higher CD values the interactions weaken enough to avoid coacervation and precipitation. Optimized examples are selected such that they are clear and have no coacervate or precipitate.

Table 2.1 describes the compositions of the visibly clear, optimized, formulations. FIG. 1 former describes some of the optimized formulations on a phase map showing the coacervation boundary.

TABLE 2.1

| ID | Ammonyx® LO wt % | Dowfax™ 2A1 wt % | Na$_2$CO$_3$ wt % | NaOCl wt % | Floquat FL4245 wt % | CD | P/D$_{net}$ | Appearance |
|---|---|---|---|---|---|---|---|---|
| B1 | 0.728 | 0.272 | 2.499 | 0.998 | 0.010 | 0.874 | −0.066 | Clear |
| B2 | 0.710 | 0.265 | 2.499 | 0.998 | 0.025 | 0.874 | −0.169 | Clear |
| B3 | 0.798 | 0.177 | 2.499 | 0.998 | 0.025 | 0.921 | −0.252 | Clear |
| B4 | 0.692 | 0.258 | 2.499 | 0.998 | 0.050 | 0.874 | −0.346 | Cloudy |
| B5 | 0.777 | 0.173 | 2.499 | 0.998 | 0.050 | 0.921 | −0.517 | Clear |
| B6 | 0.655 | 0.245 | 2.499 | 0.998 | 0.100 | 0.874 | −0.731 | Cloudy |
| B7 | 0.736 | 0.164 | 2.499 | 0.998 | 0.100 | 0.921 | −1.092 | Clear |
| B8 | 0.582 | 0.218 | 2.499 | 0.998 | 0.200 | 0.874 | −1.644 | Clear |
| B9 | 0.654 | 0.146 | 2.499 | 0.998 | 0.200 | 0.921 | −2.457 | Clear |
| B10 | 0.127 | 0.073 | 2.499 | 0.998 | 0.800 | 0.819 | −19.657 | cloudy |
| B11 | 0.146 | 0.054 | 2.499 | 0.998 | 0.800 | 0.874 | −26.306 | Clear |
| B12 | 0.728 | 0.272 | 2.499 | 0.998 | 0 | 0.874 | 0 | |

Example 3

Concentrates Suitable for Dilution

The instant invention can also provide products that are prepared as concentrates which are diluted upon, use. Since the formation of a coacervate phase is undesirable for the reasons cited above, optimization of the formulations such that coacervates are not present in both the concentrate and at the level of dilution, desired may be an important characteristic to provide. The optimization is achieved by creating a series of samples, varying the absolute value of $P/D_{net}$ via varying the concentration of the polymeric counterion at a fixed mixed micelle composition, carbonate buffer, and bleach concentration until a formulation which is free of coacervates at the desired dilution is identified. As will be readily apparent, compositions which are free of coacervate are not directly indicated by the absolute value of the P/Dnet parameter. This parameter may be modulated as described herein, and while a specific threshold value may not correspond to a division of compositions that are free of coacervate and those that are not, this parameter still represents a useful tool.

Formulations C1 through C4, although clear and free of coacervate as concentrates, appear cloudy when diluted by a factor of 5 with deionized water, and hence are not suitable for this particular dilution. The absolute value of P/Dnet for these formulations ranges from 0.007 to 0.0308. In Formulations C5 through C8, the absolute value of the P/Dnet parameter is reduced slightly, from a high of 0.0058 to a low of 0.0012, to yield concentrates that can be diluted by a factor of 5 without forming coacervates. C9 represents the control, without any Floquat 4540, the poly(DADMAC) cationic polymer.

prepared from precursor solutions which are mixed just prior to use. Such two-part formulations may be desirable for enhancing the stability of an oxidant such as sodium hypochlorite over longer-term storage, or may be desirable for use with automated dilution systems for commercial or industrial use in restaurants, hospitals, etc.

Formulation D1 is an example in which the mixed micelles comprising the amine oxide and anionic surfactant and the optional buffer comprise the first part of the two part system, while the water-soluble polymer (here poly(DADMAC), the Floquat 4540) and the sodium hypochlorite comprise the second part of the two part system. Both Part A and Part B are clear solutions, free of coacervates and precipitates. When mixed in the volumes indicated in table 4.1, the polymer-micelle complexes are formed without the appearance of coacervates or precipitates.

Formulation D2 is an alternative two-part system. Part A comprises micelles of the anionic surfactant in a solution with the sodium carbonate buffer and sodium hypochlorite. Part B comprises micelles of the nonionic amine oxide and the water-soluble polymer. Both Part A and Part B are clear solutions. When mixed in the volumes indicated in table 4.1, the surfactants re-equilibrate to form mixed micelles in the diluted solution. These mixed micelles, of course, will have a net negative charge due to the presence of the anionic surfactant (which is in excess of any cationic surfactant such as a quaternary ammonium compound), and will thus interact with, the cationic water-soluble polymer to produce the polymer-micelle complexes desired. Note that the P/Dnet parameter of the final solutions produced from, formulations D1 and D2 axe the same, and within the scope of the instant invention (i.e., both negative). The appearance of the diluted solutions produced from both formulations was checked immediately

TABLE 3.1

| ID | Ammonyx® LO wt % | Dowfax™ 2A1 wt % | Na$_2$CO$_3$ wt % | NaOCl wt % | Floquat FL4540 wt % | Appearance after 5x dilution with DI-water | P/D$_{net}$ |
|---|---|---|---|---|---|---|---|
| C1 | 0.885 | 0.205 | 2.215 | 0.828 | 0.0035 | cloudy | −0.0308 |
| C2 | 0.885 | 0.205 | 2.215 | 0.828 | 0.0009 | cloudy | −0.0077 |
| C3 | 0.885 | 0.205 | 2.215 | 0.828 | 0.0018 | cloudy | −0.0154 |
| C4 | 0.885 | 0.205 | 2.215 | 0.828 | 0.0027 | cloudy | −0.0231 |
| C5 | 0.885 | 0.205 | 2.215 | 0.828 | 0.0002 | clear | −0.0019 |
| C6 | 0.885 | 0.205 | 2.215 | 0.828 | 0.0004 | clear | −0.0039 |
| C7 | 0.885 | 0.205 | 2.215 | 0.828 | 0.0007 | clear | −0.0058 |
| C8 | 0.885 | 0.205 | 2.215 | 0.828 | 0.0001 | clear | −0.0012 |
| C9 | 0.885 | 0.205 | 2.215 | 0.828 | 0 | polymer free control; clear | 0 |

Example 4

Two Part Compositions

The polymer-micelle complexes, which exhibit superior wetting and spreading on a wide variety of surfaces, may be prepared upon preparation, and after 8 hours. The appearance both immediately after preparation and after 8 hours was unchanged, as expected, since the polymer-micelle complexes are thought to be thermodynamically favored and hence stable structures.

TABLE 4.1

| ID | | Ammonyx® LO wt % | Dowfax™ 2A1 wt % | Na$_2$CO$_3$ wt % | NaOCl wt % | Floquat FL4540 wt % | parts to mix | appearance | P/D$_{net}$ |
|---|---|---|---|---|---|---|---|---|---|
| D1 | Part A | 1.071 | 0.400 | 4.588 | | | 1.192 | clear | |
| | Part B | | | | 2.189 | 0.438 | 1 | clear | |
| | mix A + B | 0.582 | 0.218 | 2.495 | 0.998 | 0.200 | | clear | −1.644 |

TABLE 4.1-continued

| ID | | Ammonyx® LO wt % | Dowfax™ 2A1 wt % | $Na_2CO_3$ wt % | NaOCl wt % | Floquat FL4540 wt % | parts to mix | appearance | $P/D_{net}$ |
|---|---|---|---|---|---|---|---|---|---|
| D2 | Part A | | 0.325 | 3.730 | 1.493 | | 2.019 | clear | |
| | Part B | 1.758 | | | | 0.604 | 1 | clear | |
| | mix A + B | 0.582 | 0.218 | 2.495 | 0.998 | 0.200 | | clear | −1.644 |

Example 5

Mixed Micelles Comprising Anionic, Cationic, and Nonionic Surfactant with a Polymeric Counterion The mixed micelles of the instant invention may comprise mixtures of anionic, cationic, and nonionic surfactants. As taught herein, the net charge on the mixed micelles should be anionic, in order to ensure electrostatic interactions with a water-soluble polymer hearing cationic charges. Formulation E1 is an example in which the mixed micelles comprise a cationic surfactant which is a germicidal quaternary ammonium compound (Sanisol 08), an anionic surfactant (sodium octanoate, a soap), and a nonionic amine oxide surfactant (Ammonyx® MO). Formulation E1 is also an example of a formulation containing optional adjuvants that include a buffer (sodium carbonate) and a hydrotrope, sodium xylene sulfonate, in a ready to use formulation which is clear and free of coacervates and precipitates.

Sanisol has a molecular weight of 284 g/mole. Sodium octanoate has a molecular weight of 166.2 g/mole.

Poly(DADMAC)=poly(diallyl dimethyl ammonium chloride), Floquat FL4245 (SNF Corp.), supplied as 40% active solution in water, Z polymer=1, Q polymer=1, M polymer=162, F polymer=1 (homopolymer).

Sodium hypochlorite source=Clorox germicidal bleach, titrated immediately prior to use to determine the sodium hypochlorite activity.

The calculation of Dnet is done as follows:

Eq cationic=0.1×1/284=0.00035 equivalents/100 g formulation.

And $D$ cationic=(+1)×(0.00035)=+0.00035.

Eq anionic=0.08×1/166.2=4.813×10$^{-4}$ equivalents/ 100 g formulation.

And $D$ anionic=(−1)×4.813×10$^{-4}$=−4.813×10$^{-4}$.

Thus, Dnet=+0.00035+(−4.813×10$^{-4}$)=−1.3134×10$^{-4}$

The negative value of Dnet indicates that the mixed micelles will bear a net anionic charge suitable for interaction with a water-soluble polymer bearing a cationic charge as a polymeric counterion to form the polymer-micelle complexes of the instant invention.

Poly(DADMAC) is a homopolymer with a molecular weight of 161.7 grams/mole in the repeat unit, which has a single cationic charge. The polymer is present at a concentration of 0.05% in formulation E1. Thus, P can be calculated as below:

$P$=0.05×1×1×(+1)/161.7=+0.0003092

And P/Dnet is thus calculated as:

P/Dnet=+0.0003092/−0.00013134=−2.354.

The negative value of P/Dnet indicates that the mixed micelles and water-soluble polymer bear opposite charges and will thus have electrostatic interactions which drive the assembly of the polymer-micelle complexes of the instant invention. Since the absolute value of the P/Dnet parameter is greater than 1, the number of cationic charges duo to the water-soluble polymer exceeds the number of anionic charges on the mixed micelles.

TABLE 5.1

| Ingredient | Formulation E1 |
|---|---|
| sodium hypochlorite | 1% |
| Sodium carbonate | 2.50% |
| octyl dimethyl benzyl ammonium chloride (Sanisol 08) | 0.10% |
| sodium xylenesulfonate (Stepanate SXS) | 0.32% |
| sodium octanoate (Aldrich) | 0.08% |
| Myristyl dimethylamineoxide (Ammonyx MO) | 0.07% |
| Poly(DADMAC) | 0.05% |
| Eq cationic | 0.00035 |
| D cationic | +0.00035 |
| Eq anionic | 0.0004813 |
| D anionic | −0.0004813 |
| P | +0.0003092 |
| P/Dnet | −2.354 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A method for cleaning a surface, the method comprising:
contacting said surface with a composition comprising a polymer-micelle complex comprising:
a negatively charged micelle electrostatically bound to a water-soluble polymer bearing a positive charge; and
wherein said polymer does not comprise block copolymer, latex particles, polymer nanoparticles, cross-linked polymers, silicone copolymer, fluorosurfactant, or amphoteric copolymer;
wherein said composition does not form a coacervate;
wherein said composition is not applied to organic contaminants in a subsurface location; and
wherein said composition does not comprise a polyelectrolyte complex.

2. The method of claim 1, wherein the composition comprising a polymer-micelle complex is a concentrate, the method further comprising diluting the concentrate with water to form a dilute composition comprising the polymer-micelle complex, prior to contacting the surface with the dilute composition and wherein the diluted composition also does not form a coacervate.

3. The method of claim 1, wherein the composition further comprises an oxidant.

4. The method of claim 3, wherein the oxidant is selected from the group consisting of:
   a. hypohalous acid, hypohalite or sources thereof;
   b. hydrogen peroxide or sources thereof;
   c. peracids, peroxyacids, peroxoacids, or sources thereof;
   d. organic peroxides or hydroperoxides;
   e. peroxygenated inorganic compounds;
   f. solubilized chlorine, solubilized chlorine dioxide, a source of free chlorine, acidic sodium chlorite, an active chlorine generating compound, or a chlorine-dioxide generating compound;
   g. an active oxygen generating compound;
   h. solubilized ozone;
   i. N-halo compounds; and
   j. combinations thereof.

5. The method of claim 1, wherein the negatively charged micelle comprises an anionic surfactant selected from the group consisting of alkyl sulfates, alkyl sulfonates, alkyl ethoxysulfates, fatty acids, fatty acid salts, alkyl amino acid derivatives, glycolipid derivatives with anionic groups, rhamnolipid derivatives with anionic groups, sulfate derivates of alkyl ethoxylate propoxylates, alkyl ethoxylate sulfates, and combinations thereof.

6. The method of claim 1, wherein the negatively charged micelle further comprises a nonionic surfactant.

7. The method of claim 6, wherein the nonionic surfactant comprises an amine oxide.

8. The method of claim 1, wherein the composition further comprises a cationic surfactant.

9. The method of claim 8, wherein the cationic surfactant comprises a quaternary ammonium compound.

10. The method of claim 1, wherein the water-soluble polymer bearing a positive charge is made from a monomer selected from the group consisting of diallyl dimethyl ammonium chloride, quaternary ammonium salts of substituted acrylamide, methylacrylamide, acrylate and methacrylate, quaternized alkyl amino acrylate esters and amides, MAPTAC (methacrylamido propyl trimethyl ammonium chlorides), trimethyl ammonium methyl methacrylate, trimethyl ammonium propyl methacrylamide, 2-vinyl N-alkyl quaternary pyridinium salts, 4-vinyl N-alkyl quaternary pyridinium salts, 4-vinylbenzyltrialkylammonium salts, 2-vinyl piperidinium salts, 4-vinyl piperidinium salts, 3-alkyl 1-vinyl imidazolium salts, or ethyleneimine and mixtures thereof or is a water-soluble polymer selected from the group chitosan, chitosan derivatives bearing cationic groups, guar derivatives bearing cationic groups, or a polysaccharide bearing cationic groups, and combinations thereof.

11. The method of claim 1, further comprising a pH buffer.

12. The method of claim 11, wherein the pH buffer is selected from the group consisting of carbonates, phosphates, silicates, borates, and combinations thereof.

13. A method for treating a surface comprising:
   mixing a first composition comprising a water-soluble polymer bearing a positive charge wherein said polymer does not comprise block copolymer, latex particles, polymer nanoparticles, cross-linked polymers, silicone copolymer, fluorosurfactant, or amphoteric copolymer with a second composition comprising a negatively charged micelle to form a polymer-micelle complex in the resulting composition, wherein said resulting composition does not form a coacervate and wherein said resulting composition does not comprise a polyelectrolyte complex; and
   contacting said resulting composition with a surface and wherein said resulting composition treats the surface.

14. The method of claim 13, wherein at least one of the first or second compositions further comprises an oxidant.

15. The method of claim 14, wherein the oxidant is selected from the group consisting of:
   a. hypohalous acid, hypohalite or sources thereof;
   b. hydrogen peroxide or sources thereof;
   c. peracids, peroxyacids, peroxoacids, or sources thereof;
   d. organic peroxides or hydroperoxides;
   e. peroxygenated inorganic compounds;
   f. solubilized chlorine, solubilized chlorine dioxide, a source of free chlorine, acidic sodium chlorite, an active chlorine generating compound, or a chlorine-dioxide generating compound;
   g. an active oxygen generating compound;
   h. solubilized ozone;
   i. N-halo compounds; and
   j. combinations thereof.

16. The method of claim 13, wherein the negatively charged micelle comprises an anionic surfactant selected from the group consisting of alkyl sulfates, alkyl sulfonates, alkyl ethoxysulfates, fatty acids, fatty acid salts, alkyl amino acid derivatives, glycolipid derivatives with anionic groups, rhamnolipids, rhamnolipid derivatives with anionic groups, sulfate derivates of alkyl ethoxylate propoxylates, alkyl ethoxylate sulfates, and combinations thereof.

17. The method of claim 13, wherein the water-soluble polymer bearing a positive charge is made from a monomer selected from the group consisting of diallyl dimethyl ammonium chloride, quaternary ammonium salts of substituted acrylamide, methylacrylamide, acrylate and methacrylate, quaternized alkyl amino acrylate esters and amides, MAPTAC (methacrylamido propyl trimethyl ammonium chlorides), trimethyl ammonium methyl methacrylate, trimethyl ammonium propyl methacrylamide, 2-vinyl N-alkyl quaternary pyridinium salts, 4-vinyl N-alkyl quaternary pyridinium salts, 4-vinylbenzyltrialkylammonium salts, 2-vinyl piperidinium salts, 4-vinyl piperidinium salts, 3-alkyl 1-vinyl imidazolium salts, or ethyleneimine and mixtures thereof or is a water-soluble polymer selected from the group chitosan, chitosan derivatives bearing cationic groups, guar derivatives bearing cationic groups, or a polysaccharide bearing cationic groups, and combinations thereof.

18. A method for cleaning a surface, the method comprising:
   contacting said surface with a composition comprising a polymer-micelle complex comprising:
   a negatively charged micelle electrostatically bound to a water-soluble polymer bearing a positive charge; and
   wherein said polymer does not comprise block copolymer, latex particles, polymer nanoparticles, cross-linked polymers, silicone copolymer, fluorosurfactant, or amphoteric copolymer;
   wherein said composition does not form a coacervate;
   wherein said composition is not applied to organic contaminants in a subsurface location;
   wherein said composition does not comprise alcohols or glycol ethers; and
   wherein said composition does not comprise a polyelectrolyte complex.

19. The method of claim 18, wherein the negatively charged micelle comprises an anionic surfactant selected from the group consisting of alkyl sulfates, alkyl sulfonates, alkyl ethoxysulfates, fatty acids, fatty acid salts, alkyl amino acid derivatives, glycolipid derivatives with anionic groups, rhamnolipids, rhamnolipid derivatives with anionic groups, sulfate derivates of alkyl ethoxylate propoxylates, alkyl ethoxylate sulfates, and combinations thereof.

20. The method of claim 18, wherein the water-soluble polymer bearing a positive charge is made from a monomer selected from the group consisting of diallyl dimethyl ammonium chloride, quaternary ammonium salts of substituted acrylamide, methylacrylamide, acrylate and methacrylate, quaternized alkyl amino acrylate esters and amides, MAPTAC (methacrylamido propyl trimethyl ammonium chlorides), trimethyl ammonium methyl methacrylate, trimethyl ammonium propyl methacrylamide, 2-vinyl N-alkyl quaternary pyridinium salts, 4-vinyl N-alkyl quaternary pyridinium salts, 4-vinylbenzyltrialkylammonium salts, 2-vinyl piperidinium salts, 4-vinyl piperidinium salts, 3-alkyl 1-vinyl imidazolium salts, or ethyleneimine and mixtures thereof or is a water-soluble polymer selected from the group chitosan, chitosan derivatives bearing cationic groups, guar derivatives bearing cationic groups, or a polysaccharide bearing cationic groups, and combinations thereof.

\* \* \* \* \*